United States Patent
Schultz et al.

[11] Patent Number: 6,011,990
[45] Date of Patent: Jan. 4, 2000

[54] METHOD AND DEVICE FOR EVALUATING AN EEG CARRIED OUT IN THE CONTEXT OF ANAESTHESIA OR INTENSIVE CARE

[75] Inventors: Arthur Schultz; Barbara Schultz, both of Adelheidsdorf, Germany

[73] Assignee: Arthur Schultz, Adelheidsdorf, Germany

[21] Appl. No.: 09/051,905
[22] PCT Filed: Oct. 17, 1996
[86] PCT No.: PCT/DE96/01975
§ 371 Date: Apr. 17, 1998
§ 102(e) Date: Apr. 17, 1998
[87] PCT Pub. No.: WO97/15013
PCT Pub. Date: Apr. 24, 1997

[30] Foreign Application Priority Data

Oct. 19, 1995 [DE] Germany .......................... 195 38 925

[51] Int. Cl.⁷ .................................................. A61B 5/0476
[52] U.S. Cl. .................................................. 600/544
[58] Field of Search .............................................. 600/544

[56] References Cited

U.S. PATENT DOCUMENTS 4,557,270 12/1985 John .
4,869,264 9/1989 Silberstein .............................. 600/544
5,083,571 1/1992 Prichep .
5,356,368 10/1994 Monroe .................................. 600/545
5,357,976 10/1994 Feng ......................................... 600/54

FOREIGN PATENT DOCUMENTS

WO93/07804 4/1993 WIPO .

OTHER PUBLICATIONS

Biomedizinische Technik, 37, vol. 6, 1992, pp. 122–130. "Sleep Classification in Infants . . . ".

"Identification of EEG Patterns Occurring in Anesthesia by Means of Autoregressive Parameters", 1991, Biomedizinische Technik, vol. 36, pp. 236–240.

*Primary Examiner*—William E. Kamm
*Attorney, Agent, or Firm*—Collard & Roe, PC

[57] ABSTRACT

A method of evaluating an EEG carried out in the context of anaesthesia or intensive care is disclosed. To this end, parameters from the time and/or frequency domains are determined from the EEG curves, the parameters determined are used in multivariate classification functions, and on this basis the EEG carried out in the context of anaesthesia or intensive care is automatically divided into stages.

12 Claims, 4 Drawing Sheets

METHOD AND DEVICE FOR EVALUATING AN EEG CARRIED OUT IN THE CONTEXT OF ANAESTHESIA OR INTENSIVE CARE

The invention concerns a method for evaluating an EEG carried out in the context of anaesthesia or intensive care according to the precharacterizing part of claim 1 and a device for evaluating an EEG carried out in the context of anaesthesia or intensive care according to the precharacterizing part of claim 5.

Electroencephalography is a method of representing electrical activity generated by the brain. With the conventional way, registration of the EEG is by a multi-channel recorder onto reel paper, as a rule at a registration speed of 30 mm/s. The German EEG Society recommends the use of devices with at least ten channels. In order to be able to properly assess the signals from the various regions of the head, the electrodes are interconnected in various ways in several derivation programs. Increasingly, recording is also computer-assisted.

The composition of the wave shapes in the electroencephalogram (EEG) depends on the functional state of the brain. The EEG diagrams of patients in surgical and intensive-care areas are varied; they can be influenced by a large number of endogenous and exogenous factors. Apart from the normal waking state EEG, the following for example have to be expected: elements of the sleep EEG, effects of medication and other exogenously admitted chemical substances, influences due to ventilation and metabolism, temperature effects, consequences of traumatic brain lesions as well as inflammable, vascular, degenerative EEG alterations and EEG alterations caused by neoplasms.

The waves occurring in the EEG are allocated to the following frequency domains: alpha (7.5–12.5 Hz), beta (>12.5 Hz), theta (3.5–7.5 Hz) and delta (0.5–3.5 Hz).

Apart from these, the subdelta band (<0.5 Hz) and the gamma band (>30 Hz) can be delimited. During the findings, the waves in the frequency domains are described concerning their amplitude, frequency, regularity, temporal structure, local distribution and change during stimulation. EEG amplitudes are measured in $\mu V$. As a rule, waves of higher frequencies have smaller amplitudes whereas slowing down is usually accompanied by an increase in amplitude.

To classify stages of sleep EEG, anaesthesia EEG or coma EEG, Kugler proposes an EEG division in which the waking state is described by A, and EEG images with progressive depression of cerebral function are described by the letters B to F. In order to assess the EEG curves, the frequency and amplitude of the waves in certain frequency domains, as well as typical patterns, are used.

With the majority of adults, the waking EEG, stage A, is characterized by waves in the alpha frequency domain. Stage B is characterized by waves of faster frequency and lower amplitude. In the stages C or D, theta waves and delta waves occur. In stage E, the curve is characterized by high-amplitude delta activity.

Stage F is characterized by a change between flat to isoelectric curve sections and groups of higher waves; by the burst-suppression sample; or by activity which is continuously very flat.

The derivation of a conventional EEG is relatively demanding. Interpretation requires special knowledge and experience. A better judgment of the dynamically progressing EEG changes is possible by recording the original signal, and by applying EEG spectrum analysis. In order to calculate an EEG power spectrum, after analog-digital conversion, the EEG signals are subjected to a Fast Fourier Transformation (FFT) for a defined time period. By means of the Fourier transformation, the wave diagram of the EEG is divided into underlying oscillation components; there is a conversion from the temporal to the frequency domain. The squared amplitudes of the oscillation components constitute the power spectrum. The frequencies occurring in the time signal can be read from the EEG power spectrum. But this information too, requires interpretation in order to gain an insight into the EEG stage and thus into the stage of cerebral function.

In order to obtain automatic pattern recognition, it is known from the journal "Biomedizinische Technik" [Biomedical Technology], 37, vol. 6 1992, pp. 122–130, to use autoregressive parameters for classification of EEG sections. Here, classification relates to categories A, C and E. The results obtained show that autoregressive parameters have a high discrimination value and that the use of squared discrimination functions results in low rates of classification errors.

It is the object of the present invention to describe a method and a device for evaluating an EEG carried out in the context of anaesthesia or intensive care, in which all categories of the EEG stage can unambiguously be determined directly from the EEG curves, and in which influences as a result of interference can be avoided as far as possible.

This object is met by a method according to the precharacterizing part of claim 1, by the marked features stated in the characterizing part of claim 1 and by a device according to the precharacterizing part of claim 6, by the marked features stated in claim 6.

EEG signals are stochastic processes, i.e. random processes, which can be approximated by means of mathematical-statistical statistical methods. For practical reasons it is desirable, for further computer processing of the EEG, to achieve a reduction to a few parameters only, which are as meaningful as possible. Parameter formation can take place either in the time domain or in the frequency domain. The EEG signal forms the data basis for analyses in the time domain; prior to calculations in the frequency domain, the data is transformed.

Fourier analysis is one option of analysing EEG signals in the frequency domain. By means of the Fourier transformation, the complex wave diagram of the EEG is divided into the underlying oscillation components, followed by a translation from the time domain into the frequency domain. The squared amplitudes of these oscillation components form the so-called power spectrum. Further processing of the results of the Fourier analysis comprises the extraction of so-called spectrum parameters as well as continued statistical calculations. Parameters which can be derived from the spectrum include for example the total power as well as absolute and relative power in different frequency bands. The median, the spectral edge frequency, and the dominant frequency are further frequently used parameters. The median is the frequency at which the area of the spectrum is divided into two equal parts. The spectral edge frequency is most often defined as the 95% quantile, i.e. 95% of the total power of the spectrum is below this frequency. The dominant frequency is the frequency with the highest power.

By means of the power spectrum, the frequency distribution of EEG sections can be presented clearly. However, most of the time, it is not possible to use the spectrum to infer special patterns such as burst-suppression phases or the potential of suffering a fit.

The fast Fourier transformation (FFT) is one method for quickly calculating the power spectrum.

The determination of autoregressive parameters is one option for analysing EEG signals in the time domain. Autoregressive (AR) parameters are values from the time domain. A measured value at a specified point in time is represented as a weighted sum of its historic values plus a random component. The AR parameters form the weighting. The general formula for an AR process is as follows:

$$Y_t = a_1 * Y_{t-1} + \ldots + a_p * Y_{t-p} + e_t.$$

In this, $Y_t$ designates the measured value at the time t; $a_i$, $i=1, \ldots, p$ the AR parameters, and $e_t$ independent random components with an average value of 0 and constant variance for all time points t. The letter p designates the order of the process, i.e. the number of historical values that need to be taken into account. The model parameters can be estimated using the Yule-Walker equations. Determining the order of the model and checking the quality of the model is usually according to Box and Jenkins. Kay and Marple provide an overview of further methods of estimation and model categories.

The calculation of special EEG parameters, proposed and named after Hjorth, is a frequently used method for characterizing EEG measurements. It involves the three parameters: activity, mobility and complexity. The Hjorth parameters are calculated from the scatter of the EEG signal, as well as from their first and second derivation. As an alternative, calculation of the Hjorth parameters can also take place in the frequency domain, i.e. by means of the spectrum analysis.

The activity corresponds with the total power of the signal and is thus a measure of the extent of the amplitude of the EEG measurement. Mobility can be interpreted as a measure for the middle frequency; and complexity as a measure for the variability of the signal.

Apart from pure spectrum parameters or pure AR parameters, the combined determination of spectrum parameters, AR parameters. Hjorth parameters or also chaos parameters is possible.

For example discrimination-analysis methods or neuronal nets are suitable for classifying EEG data by means of multivariate classification functions based on spectrum parameters and/or AR parameters and/or Hjorth parameters and/or chaos parameters.

Discrimination-analysis classification methods are suitable for classifying objects into one of several defined groups, by means of a number of elevated characteristics. In the case of division into stages of the anaesthesia EEG or the intensive-care EEG, the EEG sections form the objects to be classified which are characterized by spectrum parameters and/or AR parameters and/or Hjorth parameters and/or chaos parameters. A number of methods exist for calculating suitable classification functions; these methods allow a distinction between parametric and non-parametric attempts. Classification function based on the characteristic values can be derived by means of a random sample of objects which are known to belong to a particular group. It is a prerequisite of parametric methods that the characteristic vector in the various groups follows a multivariate normal distribution. Linear discrimination analysis presupposes equality of the covariance matrixes within the individual groups; quadratic discrimination analysis makes it possible to take into account differing covariance matrixes of the groups. The Mahalanobis distance is used as a distance measure; it represents the weighted distance of an observation vector to the mean values of the group. An object is then allocated to that group in which a function, depending on the method selected, of the Mahalanobis distance, is the lowest.

If the distribution of the characteristic vector is unknown or not subject to normal distribution, then it is possible to use non-parametric methods for deriving classification rules. The k-nearest-neighbour method is an illustrative example of this. In this, the distances of the characteristic vector to be classified, to all other characteristic vectors of the random sample available, are formed, and sorted according to size. Then the observation vectors with the k smallest distances are determined. In doing so, the number k of the values taken into account must be determined beforehand. Then a determination is made as to which groups these k values belong, and their share in the total number of measurements in the individual groups is determined. Allocation is then to that group in which this share is highest.

Compared to parametric methods, this non-parametric method requires increased calculation effort, because for classification of an object it is necessary to go back to the entire original data record. In contrast, with parametric methods, the characteristic values of an object are used in classification functions.

In order to determine the quality of a classification method, the respective error rate can be used. Error rate means the share of misclassifications. Reclassification of data provides one option for estimating the error rate. The error rate determined in such a way does however provide too positive an estimate of the true error rate. A more realistic estimate of the error rate can be obtained if the classifications are checked against an independent data record. This can take place by splitting up a given data record into a training data record for deriving the classification rule and into a test data record for validating the classification. The so-called cross validation or leave-one-out method is an extreme form of splitting-up data. In this, each time, one observation is removed from the data record, and classification is made on the basis of the discrimination function from the remaining data.

If there is a large number of potential characteristics for deriving discrimination functions, then, by means of suitable step-by-step methods those parameters can be determined which ensure the highest possible separation of the groups. To this purpose, the literature suggests a number of methods; for example step by step, parameters are incorporated in the evaluation which, on the basis of Wilks Lambda, make the greatest contribution to group separation.

The division into stages of the anaesthesia EEG or the Intensive care EEG can take place based on Kugler who, as mentioned in the introduction, designates the waking state by A and the very deep depression of cerebral function by F. In this, the intermediate stages B to E can be still further subdivided, as shown in Table 1.

TABLE 1

| STAGE | LEADING EEG CHARACTERISTICS | BEHAVIOUR |
|---|---|---|
| $A_0$ | Alpha okz. standard variant | Waking state |
| $A_1$ | Alpha diffusion | Subvigilance |
| $A_2$ | Alpha low, sparse, slow Theta low | |
| $B_0$ | Theta low | Sleepiness |
| $B_1$ | Alpha occasional | or |
| $B_2$ | Theta low to medium Theta medium | very flat anaesthesia |
| $C_0$ | Theta high 30% of the time | Light sleep |
| $C_1$ | Theta high 50% of the time | or |
| $C_2$ | Theta high, slow, continuous | flat anaesthesia |
| $D_0$ | Delta up to 30% of the time | Medium sleep |
| $D_1$ | Delta up to 50% of the time | or |

TABLE 1-continued

| STAGE | LEADING EEG CHARACTERISTICS | BEHAVIOUR |
|---|---|---|
| $D_2$ | Delta up to 80% of the time | medium anaesthesia |
| E | Delta continuous | Deep sleep or deep anaesthesia |
| F | Periodically slow groups/ flat stretches | Coma or very deep anaesthesia |

Other divisions into stages, or scales of stages, may also be used.

The described method and device makes possible automatic and computer-controlled division into stages of the anaesthesia EEG or the intensive-care EEG; a task which was previously undertaken visually by means of the EEG curves. This has the advantage that there is uniform division into stages, free of errors as a result of different individual assessment. The method and device are equally suited for the monitoring of anaesthesia patients and intensive care patients in the clinical area as well as in the pharmaceutical industry during development and testing as well as when determining dosing rates of new narcotics and sedatives.

While with conventional measures only the stages A to E can be positively recognised, the determination of additional limit values of the parameters, in particular the signal power in relation to a zero line, and a correction of the multivariate classification by means of the limit values, allow a significant improvement in recognising stage F of the stage division. Since, in contrast to the other stages, this stage can partly be characterized by a zero line, the exclusive evaluation of spectral parameters, AR parameters, Hjorth parameters or chaos-parameter parameters does not always lead to a positive recognition of stage F.

Since the electrical activity generated by the brain represents a very small electrical potential, an EEG is extremely interference-prone. Essentially, EEG curves are influenced by movement artefacts, muscle artefacts or interference radiation. These interferences can on the one hand at times render the evaluation of an EEG altogether impossible; and on the other hand they can also fake electrical activity which does not originate in the brain and which would thus lead to misinterpretation.

If movement artefacts occur, for example during an operation in the presence of medical personnel, then incorrect division into stages can of course be ignored if the movement is detected. During recording of the EEG and later evaluation it is however no longer possible to determine from the EEG curve, whether or not certain signals were caused by movement artefacts.

By determining additional movement artefacts, independent of the EEG recording, the division into stages can be corrected or suppressed by means of the movement artefacts.

A further improvement of the division into stages is achieved if the age-specific classification functions for an experimentee are selected from stored differing age-dependent classification functions. It has been found that the EEG of a person contains age-dependent characteristics. To express it in a simplified way, for example, with increasing age, in the waking state the spectrum of adults shifts to lower frequencies; during anaesthesia, the delta power for example is reduced. By taking into account age-specific classification functions, correct division into stages can be made more reliably.

Furthermore it is also possible to select, from stored different medication dependent classification functions, the specific classification functions for a medication used. It has been shown that different sleep-inducing medication, that is to say narcotics or sedatives, results in different EEG curves in individual stages. In the case of classification functions selected on an overall basis, this could lead to misinterpretation and thus to an incorrect allocation of the division into stages of the anaesthesia EEG or intensive-care EEG. By taking into account specific classification functions for a particular medication used, such misallocations can be avoided.

In order to determine movement artefacts, a movement sensor, coupled to an evaluating computer, with at least one sensor element being attached to the head of the patient or experimentee, can be provided. Acceleration transducers and/or displacement transducers are particularly well suited as sensor elements.

But the sensor elements can also be electrical lines coupled to the head of the patient or experimentee; the said lines being situated in a magnetic field and/or an electrical field. During movements of the lines in the field and/or changes in the field strength, under the influence of adjacent moving bodies or objects, in the lines, currents are then induced and/or voltages are generated which can be evaluated.

In addition, muscle artefacts can also be determined from the time and/or frequency domain of the EEG curves and, by means of the muscle artefacts, the division into stages can be corrected or suppressed. Such muscle artefacts can be caused by the forehead muscles and facial muscles; they are usually recognisable in that apart from other frequency shares there are also frequency shares greater than 30 Hz.

Finally it is also possible to determine additional artefacts resulting from interference-radiation of electro-medical apparatus, in particular electrosurgical apparatus. By means of the interference-radiation artefacts, the division into stages can be corrected or suppressed. In this case, an interference-radiation sensor is provided which acquires the interference radiation.

But artefacts can also be recognised by way of software queries.

Below, the invention is illustrated by means of one embodiment, which is shown in the drawing, as follows.

Figure 1:
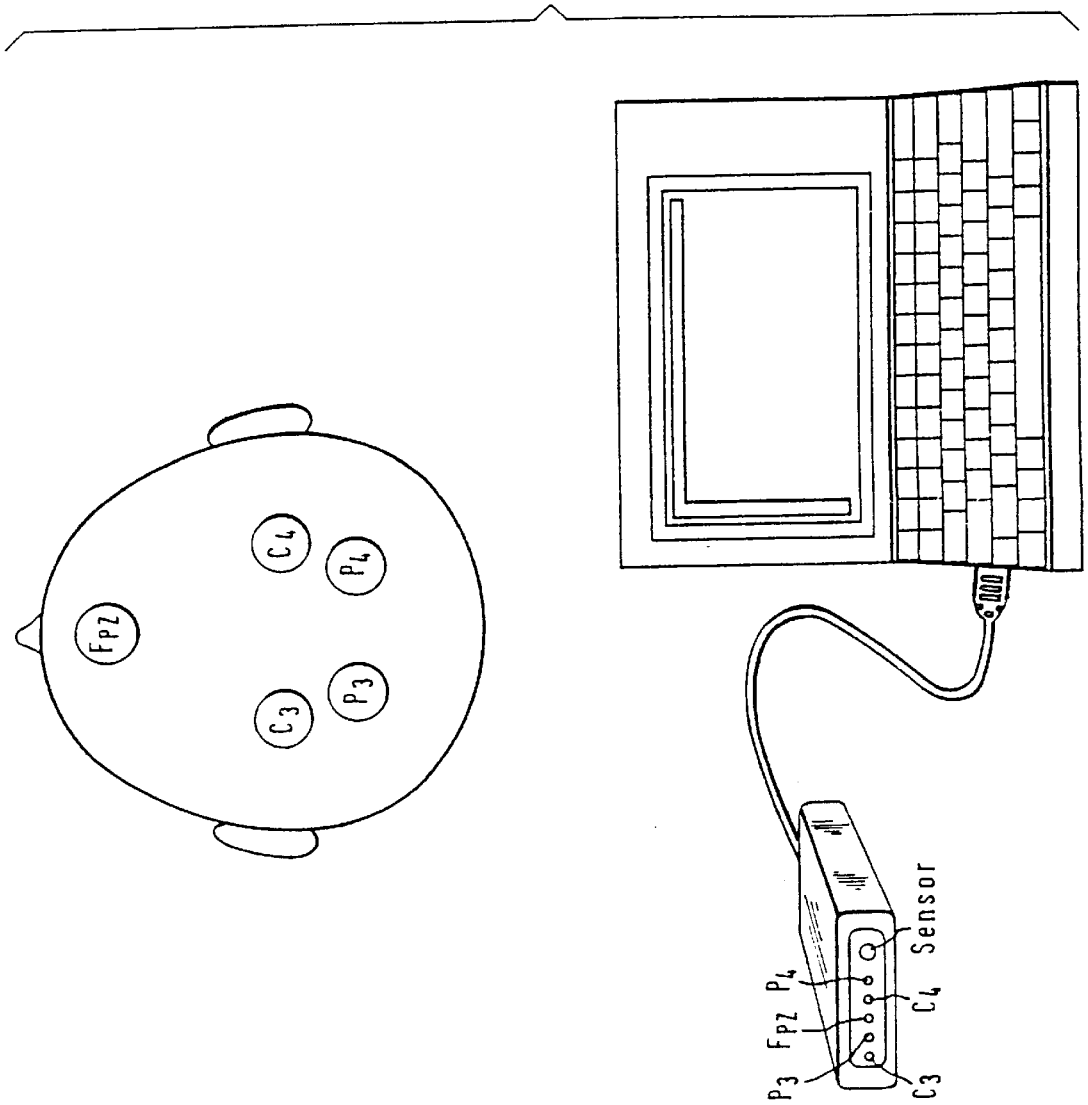
FIG. 1 shows a device comprising a personal computer and a measuring device for two EEG channels.

The device shown in FIG. 1 comprises a personal computer with colour monitor and a measuring device for two EEG channels. For EEG registration, the electrodes are attached to the head of the patient and connected to the pre-amplifier placed in the immediate vicinity of the patient. Formation of the difference between the potentials of two electrodes takes place in a difference amplifier. The signals are amplified by a factor of 20,000 in order to undertake a range of value adjustment to the AD (analog/digital) converter.

In order to detect movement artefacts, a movement sensor is attached to the patient's head. The signals of the said movement sensor are also subjected to AD conversion.

Prior to AD conversion, a high-pass and low-pass filtration as well as a notch filtration are carried out. A 50 Hz notch filter counteracts mains-hum artefacts. The filtered and amplified analog signals are digitalised at 128 Hz. This is controlled by a micro controller which makes the values available to the PC for further processing. This PC handles storage and evaluation of the data. EEG analysis takes place parallel to the AD conversion whereby continuity of the data acquisition is ensured.

After switching on the device, a selection menu appears on screen, offering the option of starting the measuring program or reading-in a measurement already stored. Keying-in can be by integrated plastic-foil keyboard, touch screen or by an external keyboard, according to choice. Output is by way of the monitor and, as an option, by way of a printer.

Prior to each measurement, the age of the patient is keyed in. As desired, the data can be evaluated, from one derivation or from two derivations, and stored.

Figure 2:
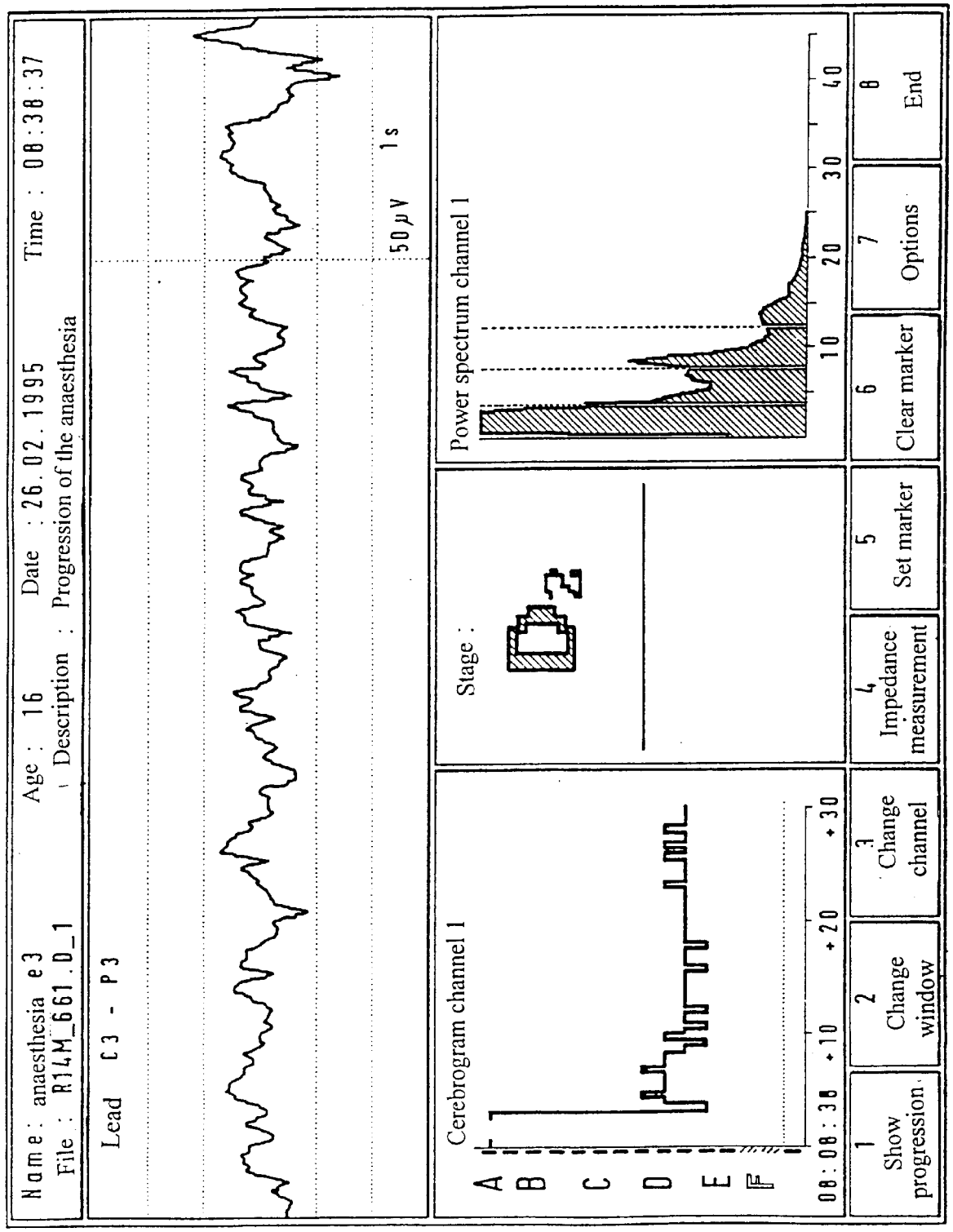
FIG. 2 shows a screen image.

From the start of the measurements, as shown in FIG. 2, the monitor continuously shows, as a cerebrogram, the original EEG of one or two derivations, an EEG power spectrum averaged from ten two-second epochs with designation of the borders of the conventional EEG frequency bands, the current stage (from A to F) and the stage progression.

In addition, the file name, the patient's age, date and time of the day, as well as, optionally, comments are issued.

Instead of the power spectrum, it is also possible to represent trends of quantiles of the power spectrum as well as of the relative power of the alpha, beta, theta and delta bands in cumulative form.

Stage classification is accomplished by means of discrimination-analysis functions as well as supplementary limit value queries. In addition, algorithms were programmed for improving the burst-suppression-phase recognition (stage F). Two-second epochs, which can be considered as burdened by artefacts, are not taken into account during classification into stages.

k stages as well as a p-dimensional characteristic vector $X=(X_1, \ldots X_p)$ (e.g. p suitable EEG parameters) provide the starting point for the compilation of discrimination-analysis functions. Allocation to one of the k stages is based on the characteristic vector X.

The derivation of classification functions with which allocation takes place is by means of a training data record. The training data record contains EEG signals, typical for the various stages. From this, classification functions for the k stages are calculated by means of discrimination-analysis methods.

In the case of classification, parameters (e.g. spectrum parameters, AR parameters, Hjorth parameters or chaos parameters) are calculated from the EEG section viewed, and inserted into the classification functions determined from the training data record. The classification functions provide an allocation probability for each of the k stages, i.e. a measure for the similarity of the viewed EEG section to the various stages. The EEG section is then allocated to the stage with the largest allocation probability.

EXAMPLE

This is to show the procedure during discrimination analysis, by means of a concrete example.

Figure 3A:
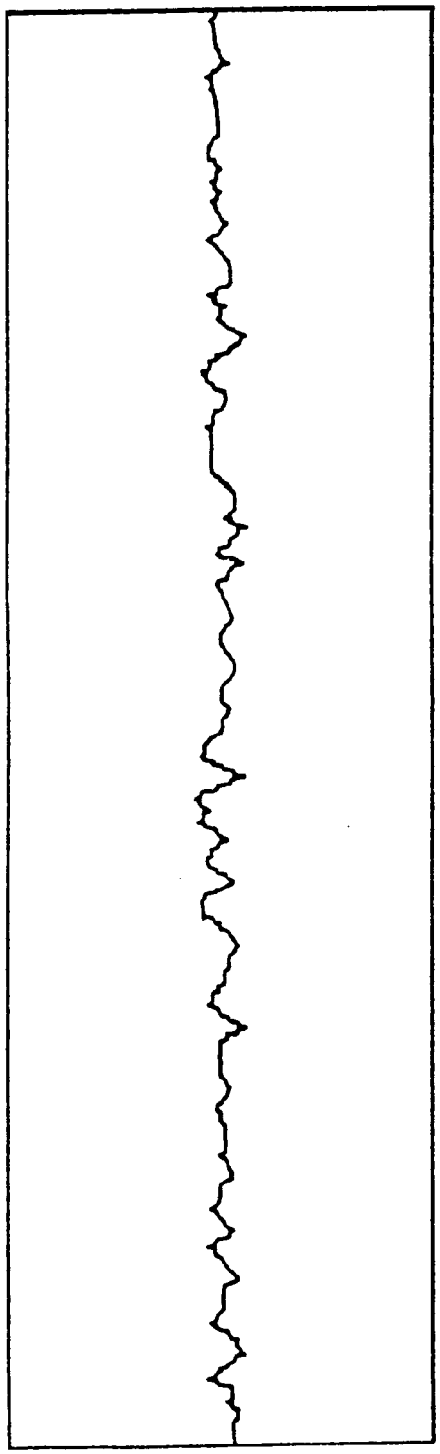
FIG. 3 is a graphical representation of two EEG sections.
Figure 3B:
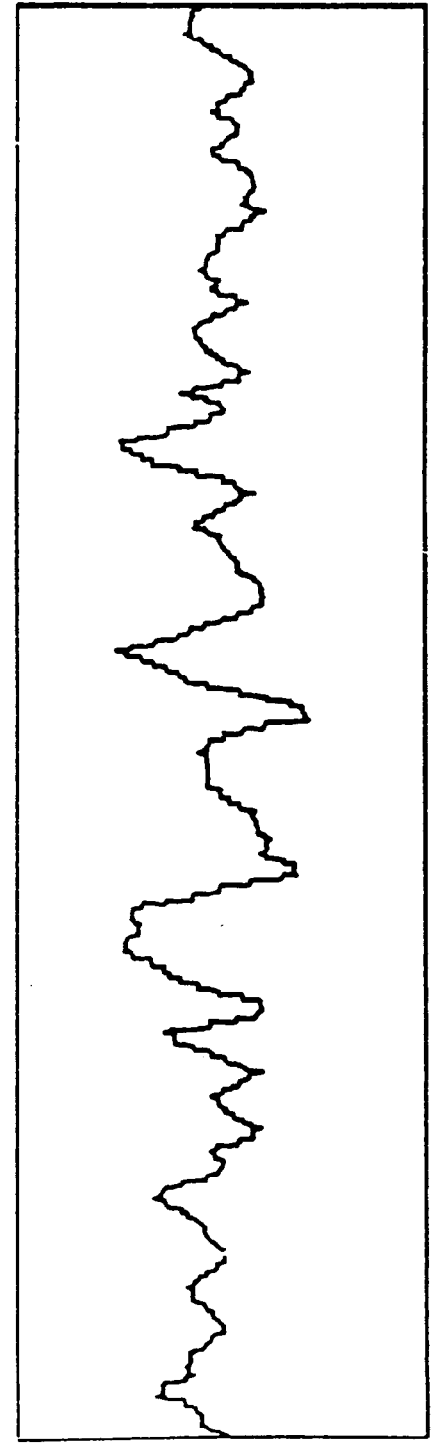
Figure 4:
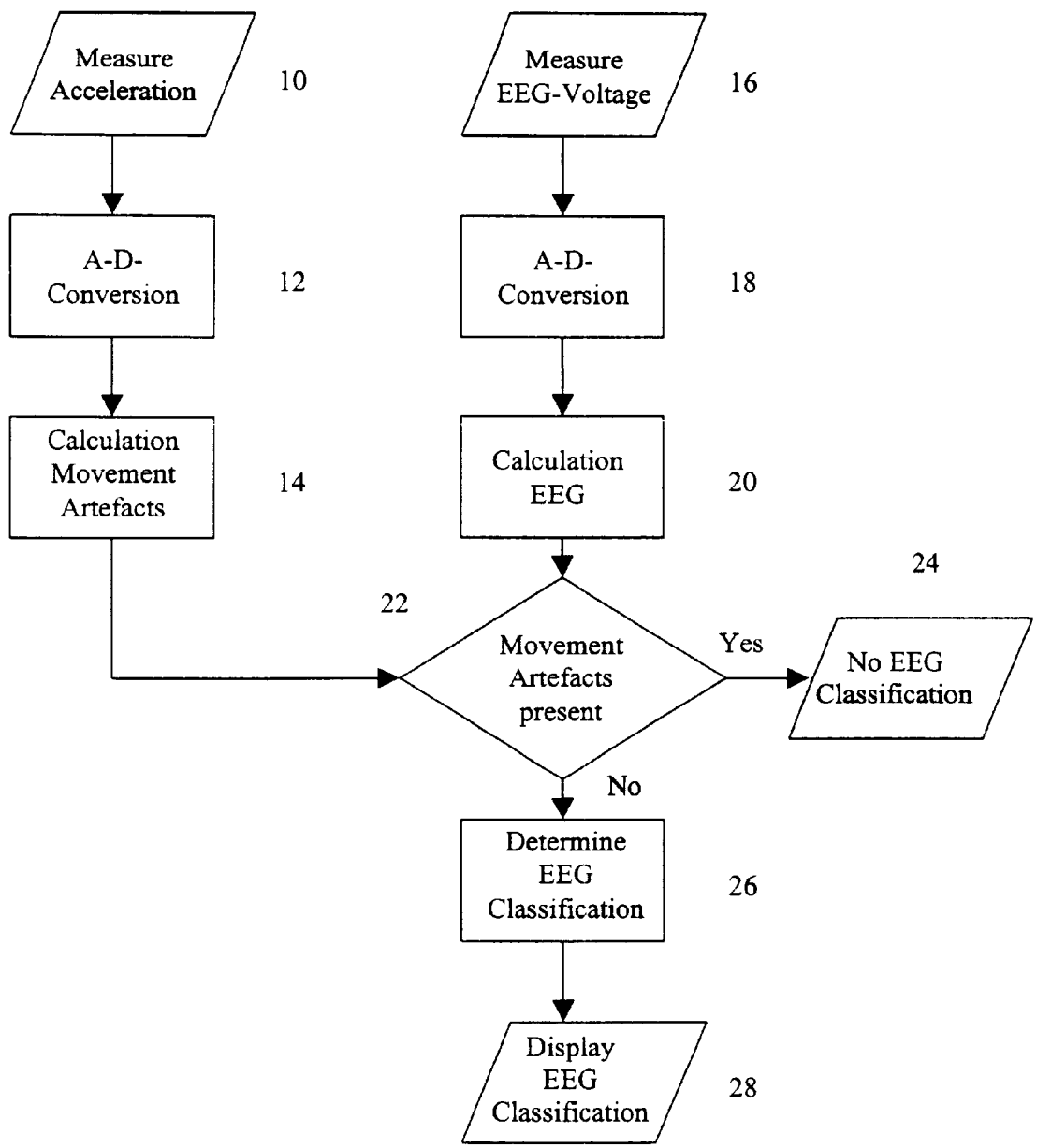
FIG. 4 is a flow diagram illustrating the method of the present invention.

The EEG sections of 2 seconds duration each, as shown in FIG. 3, are given. By means of discrimination analysis, these sections are to be allocated to a stage from A (waking) to E (deep anaesthesia). Division into stages was undertaken according to Kugler. Section (a) is an EEG section from shallow anaesthesia; section (b) an EEG from deeper anaesthesia.

The first step consists of calculating suitable parameters for characterizing the respective EEG section. In this case five autoregressive parameters as well as the logarithmic standard deviation, which corresponds to the power of the EEG signal, were calculated. It is however also possible to use other parameters, e.g. spectrum or Hjorth parameters. An EEG section is also described by the characteristic vector X, containing as components the above-named six EEG parameters.

Subsequently, the discrimination functions are calculated by means of the training data record for which the stage classification is known due to visual evaluation. In the present case, the linear discrimination analysis for 12 stages A, $B_0$, $B_1$, $B_2$, $C_0$, $C_1$, $C_2$, $D_0$, $D_1$, $D_2$, $E_0$ and $E_1$ was used.

For a concrete classification of an EEG section to be classified anew, first of all the respective characteristic vector X is calculated. For the present two EEG sections (a) and (b), one arrives at the following results:

(a) X=(1.20, 1.45, −0.89, 0.14, 0.06, 0.03), (b) X=(2.32, 1.69, −0.96, 0.18, 0.05, −0.06), wherein the first component designates the logarithmic standard deviation of the signal and the further components represent the five autoregressive parameters.

These values are then inserted into the present classification functions, and for each of the possible stages the respective allocation probability is arrived at. The values calculated for the EEG sections (a) and (b) are shown in Table 2. Classification is to that stage which most closely resembles the EEG section, i.e. the stage with the highest allocation probability. Table 2 shows that EEG section (a) is allocated to stage $B_1$; and section (b) is allocated to stage $D_0$.

TABLE 2

| | Allocation probabilities for the EEG sections from FIG. 3 Allocation probabilities for the stages | | | | | | | | | | | |
|---|---|---|---|---|---|---|---|---|---|---|---|---|
| Section | A | $B_0$ | $B_1$ | $B_2$ | $C_0$ | $C_1$ | $C_2$ | $D_0$ | $D_1$ | $D_2$ | $E_0$ | $E_1$ |
| (a) | 0.00 | 0.25 | 0.69 | 0.04 | 0.02 | 0.00 | 0.00 | 0.00 | 0.00 | 0.00 | 0.00 | 0.00 |
| (b) | 0.00 | 0.00 | 0.00 | 0.00 | 0.01 | 0.11 | 0.31 | 0.38 | 0.19 | 0.00 | 0.00 | 0.00 |

We claim:

1. A method for evaluating an EEG of a person under anaesthesia or in intensive care comprising:
    (a) measuring EEG curves of the person through a plurality of stages;
    (b) determining time or frequency domain parameters from the measured EEG curves;
    (c) inserting the determined parameters into multivariate classification functions;
    (d) automatically allocating said functions into the stages of the EEG;
    (e) determining limit values of the parameters, including EEG signal strength in relation to a base line and correcting the multivariate classification functions using the limit values;
    (f) determining movement artifacts caused by movements during the EEG; and
    (g) suppressing allocation into stages based on an evaluation of the movement artifacts.

2. A method according to claim 1 further comprising selecting age-specific classification functions for the person from age-dependent classification functions stored in a computer memory.

3. A method according to claim 1 further comprising selecting medication-specific classification functions from medication-dependent classification functions stored in a computer memory.

4. A method according to claim 1 further comprising determining muscle artifacts from the time or frequency domain parameters of the EEG curves and suppressing the allocation into stages based on an evaluation of the muscle artifacts.

5. A method according to claim 1 further comprising determining additional artifacts resulting from interference radiation from an electromedical apparatus and suppressing the allocation into stages based on an evaluation of the interference-radiation artifacts.

6. A device for evaluating an anaesthesia EEG or an intensive-care EEG of a person comprising
   (a) a measuring device for measuring EEG curves of the person through a plurality of stages;
   (b) a movement sensor having at least one sensor element adapted to be attached to or coupled with the head of the person for determining movement artifacts; and
   (c) a computer coupled to the measuring device and the movement sensor, said computer comprising:
      (i) means for determining time or frequency domain parameters from the measured EEG curves;
      (ii) means for inserting the determined parameters into multivariate classification functions;
      (iii) means for automatically allocating said functions into the stages of the EEG;
      (iv) means for determining limit values of the parameters, including EEG signal strength in relation to a base line, and for undertaking a correction of the multivariate classification function using the limit values; and
      (v) means for evaluating movement artifacts determined by the movement sensor in order to suppress the allocation into stages of the EEG.

7. A device according to claim 6 wherein the computer further comprises storage means for storing age-dependent classification functions and means for selecting age-specific classification functions from the stored classification functions by entering an age.

8. A device according to claim 6 wherein the computer further comprises storage means for storing medication-dependent classification functions and means for selecting classification functions specific to a medication used on the person from the stored classification functions by entering information about the medication.

9. A device according to claim 6 wherein the sensor element is an acceleration transducer or a displacement transducer.

10. A device according to claim 6 wherein the sensor element comprises electrical lines coupled to the head of the person, said lines being situated in a magnetic or electrical field and further comprising means for evaluating currents induced or voltages generated by said lines from movements in the field or changes in field strength.

11. A device according to claim 6 wherein the computer further comprises means for evaluating muscle artifacts from the time or frequency domain parameters of the EEG curves in order to suppress the allocation into stages of the EEG.

12. A device according to claim 6 further comprising an interference-radiation sensor coupled to the computer and wherein the computer further comprises means for evaluating interference radiation from an electromedical apparatus sensed by said interference-radiation sensor in order to suppress the allocation into stages of the EEG.

* * * * *